United States Patent [19]

Nightingale

[11] 4,159,659
[45] Jul. 3, 1979

[54] ELECTRICAL MARKING DEVICE

[76] Inventor: Carol Nightingale, Rte. #2, Box 159, Taneytown, Md. 21787

[21] Appl. No.: 906,657

[22] Filed: May 16, 1978

[51] Int. Cl.$^2$ .................... B41B 1/00; A61B 17/20
[52] U.S. Cl. ...................... 81/9.22; 30/362; 128/253
[58] Field of Search .............. 30/362, 366; 81/9.22; 128/253

[56] References Cited

U.S. PATENT DOCUMENTS

| | | | |
|---|---|---|---|
| 196,747 | 11/1877 | Edison | 30/362 |
| 464,801 | 12/1891 | O'Reilly | 81/9.22 |
| 768,413 | 8/1904 | Wagner | 81/9.22 |
| 1,724,812 | 8/1929 | Waters | 81/9.22 |
| 2,588,623 | 3/1952 | Eliscu et al. | 128/253 |
| 2,840,076 | 6/1958 | Robbins | 128/253 |

*Primary Examiner*—James G. Smith

[57] ABSTRACT

An electric marking device for tattooing humans, animals, and for other applications comprises a frame assembly having a rectangular prismatic base and a pair of side plates secured to opposite sides of the base, an electromagnet assembly mounted on the base between the side plates, an armature assembly adjustably mounted between the side plates above the electromagnet assembly, an interrupter switch supported between the side plates above the armature assembly, a needle guide assembly holder pivotally supported to the front of the base, a locator key slot provided in the needle guide assembly holder, a tubular needle guide assembly including a central tubular handpiece and upper and lower tubular extensions, a positioning collar secured on the upper extension in predetermined position, a locator key secured to the positioning collar, the needle guide assembly being removably assembled with the needle guide assembly holder in predetermined position by mating the locator key of the positioning collar with the locator key slot of the needle guide assembly holder, a needle assembly bearing block attached to the front end of the armature assembly, and a needle assembly having a needle shaft slidably mounted in the needle guide assembly with marker needles projecting from the lower end of the needle guide assembly and with a needle holder removably secured to the opposite end of the needle shaft from the marker needles, the needle holder having projecting stub shafts pivotally supported by the needle assembly bearing block.

18 Claims, 9 Drawing Figures

[4,159,659]

ELECTRICAL MARKING DEVICE

BACKGROUND OF THE INVENTION

1. Field of the Invention

This invention relates to an improved electric marking device for tattooing and for other marking applications including engraving of certain materials such as plastics, leather and metals and the marking of animals. The invention also lends itself to medical applications such as the subcutaneous or interdermal injection of pigments, medical solutions and other cosmetic or therapeutic materials.

2. Discussion of the Prior Art

Tattooing machines and surgical instruments for intradermal or subcutaneous injection of fluids known in the prior art are shown in the following representative patents:

| | | |
|---|---|---|
| 196,747 | Edison | Nov. 6, 1877 |
| 464,801 | O'Reilly | Dec. 8, 1891 |
| 768,413 | Wagner | Aug. 23, 1904 |
| 1,724,812 | Waters | Aug. 13, 1929 |
| 2,588,623 | Eliscu et al | Mar. 11, 1952 |
| 2,840,076 | Robbins | June 24, 1958 |

The efficiency and usefulness of an electric marking device for tattooing and other functions involving the injection of fluids intradermally or subcutaneously into a living being is dependent upon the adaptability of the device to be cleaned and sterilized either in its entirety or else in parts. The parts requiring sterilization must be capable of easy removal and reassembly to avoid waste of an operator's time, and they must be capable of reassembly in precise alignment with the parts to which they are connected to avoid tedious realignment procedures. Other important qualities of an efficient tattooing instrument are its light weight, balance, stroke adjustability, unobstructed view of the tattooing needles, and capability of rinsing the needle assembly between colors. This invention seeks to provide improvements in all of the aforenamed qualities in ways subsequently to be described.

SUMMARY OF THE INVENTION

It is an object of this invention to provide an improved electric marker device and more particularly an improved tattooing machine which is adaptable for other markings and fluid injection functions.

It is an important object of the invention to provide an improved tattooing machine which allows the operator to change the needle assembly and needle guide assembly between each tattoo and still maintain precision work.

It is another object of the invention to provide an electromagnet operated tattooing machine which has a unique type armature bar that improves the precision of the machine.

It is another object of the invention to provide an electromagnet operated tattooing machine which includes a leaf spring support for the armature bar and which includes a set of leaf springs of different lengths so that the operator may choose the leaf spring which best suits his needs.

It is a further object of the invention to provide an improved instrument frame which has a dual track system which permits the operator to adjust the position of the armature spring support to accommodate armature springs of different lengths and which permits the operator to adjust the position of the stationary contact of an interrupter switch that is actuated by movement of the armature.

It is another object of the invention to provide a set of leaf springs of different lengths which may be used interchangeably to support the moving contact of the interrupter switch in cantilever manner from the armature bar.

It is still another object of the invention to provide a marker needle assembly holder which is removably and pivotally supported from the armature bar, and which provides means for adjustable securing the marker needle assembly in the holder.

It is still another object of the invention to provide a needle guide assembly holder which is pivotally supported on the base of the instrument frame.

It is still another object of the invention to provide the needle guide assembly holder with locator means for precisely locating a needle guide assembly in the holder, the needle guide assembly having cooperative locating means.

It is still another object of the invention to provide the apparatus with different marker needle assemblies and with different needle guides for use interchangeably for different marking functions.

BRIEF DESCRIPTION OF THE DRAWINGS

With the foregoing more important objects and features in view and such other objects and features which may become apparent as this specification proceeds; the invention will be understood from the following description taken in conjection with the accompanying drawings, in which like characters of reference are used to designate like parts, and in which.

DETAILED DESCRIPTION OF THE PREFERRED EMBODIMENT

Figures 1, 2:
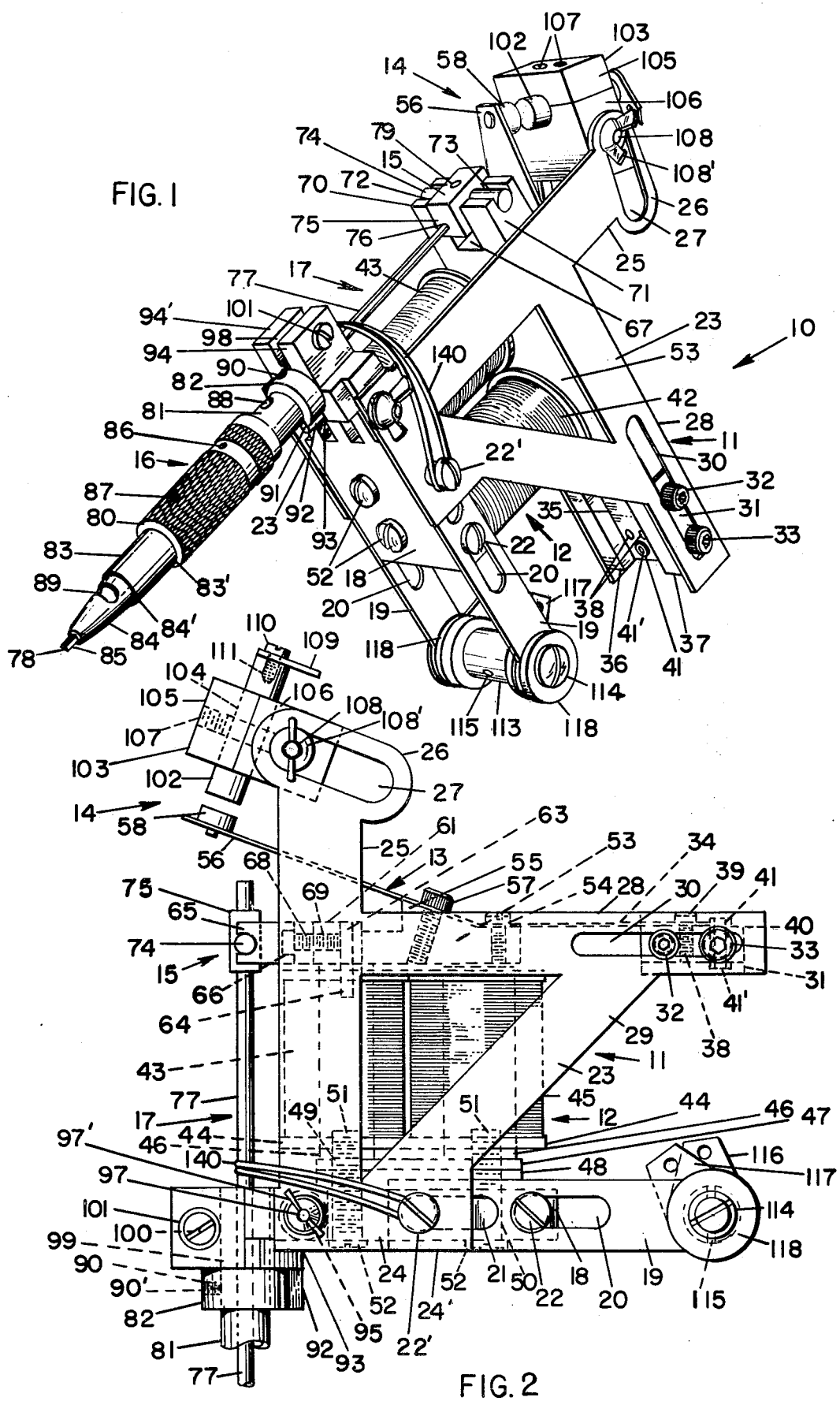
FIG. 1 is a perspective view of the electric marking device of this invention.
FIG. 2 is a partial side elevational view of the electric marking device of this invention.

The tattooing apparatus 10 of this invention is generally indicated in the drawings by the reference numeral 10. Now looking particularly at FIG. 1, the major components or subassemblies of the apparatus as indicated by arrows are a frame assembly 11, an electromagnet assembly 12, an armature assembly 13, an interrupter switch assembly 14, a needle holder assembly 15, a needle guide or handpiece assembly 16, and a needle assembly 17 of which there may be several different types from which the operator selects one for performing special tattooing functions.

The frame assembly 11 includes a rectangular prismatic base 18 on the top of which the electromagnet assembly 12 is mounted. A pair of elongated flat rear extension plates 19,19 are adjustably mounted along opposite sides of the base 18 to extend rearwardly from the base and parallel to each other and to the opposite sides of the base to which they are respectively contiguous. Each of the plates 19 include a pair of longitudinally aligned elongated slots 20,21, and a circular aperture (not shown) located at the rear end thereof. The rear extension plates 19,19 are adjustably secured to the base 18 by means of headed machine screws 22,22' or other suitable fasteners which pass through the slots and are screwed into threaded apertures (not shown) provided in the base 18. When the screws 22,22' are loosened the extension plates 19,19 may be extended rearwardly or moved forward within the confines of the slots 20,21. Tightening the screws 22,22' locks the extension plates 19,19 in adjusted position. A pair of side plates 23,23 are secured to opposite side of the base 18 outside of the rear extension plates 19,19. The same headed screw 22' which extends through the slot 21 of the rear extension plate extends through an aperture in the side plate 23 and when tightened secures the side plate 23 and rear extension plate to the base. The side plates 23,23 are designed to provide the required strength with minimum weight therefore they are each cut to provide an open work plate. Each plate 23 includes a base portion 24 having a bottom edge 24' which is parallel to the bottom of the base 18, an upstanding front strip 25 having a top elongated enlargement 26 in which there is an elongated slot 27 formed therein, a top string 28 extending rearwardly perpendicular to the front strip 25 intermediate the enlargement 26 and the base portion 24, and a diagonal strip 29 inclined rearwardly and upwardly from the base portion 24 to the top strip 28. An elongated longitudinal slot 30 is formed in the top strip 28 adjacent to the rear end thereof. A spring support 31 is adjustably secured between the top strips 28,28 of the side plates 23,23 by headed screws 32 and 33 provided on each side of the spring support extending through the slots 30 of the side plates 23 into threaded apertures provided in the spring support. The diameter of the forward screw 32 is substantially smaller then the width of the slot 30 so that the front of the spring support can be tilted upwardly or downwardly to increase or decrease the tension on the rear spring 34 mounted on top of the spring support. The diameter of the rear screw 33 is approximately equal to or slightly smaller than the width of slot 30 so that the rear screw when loosened forms a pivot about which the front of the spring support 31 may tilt. The spring support 31 may be adjusted forward or rearward, when the screws 32 and 33 on each side thereof are loosened, within the confines of the slot 30. It is secured in adjusted position by tightening the screws 32,33.

The spring support 31 is preferably made of solid light weight metal such as magnesium, however it may be made of a plastic material. It includes a recessed central portion 35 of uniform rectangular cross section and opposite end portions 36 and 37, also of uniform rectangular cross section which provide right angle top and bottom end flanges relative to the central portion 35. A pair of threaded holes 38,38 are provided in inwardly spaced parallel alignment with the front edge of the spring support 31 for receiving a pair of screws 39,39 for attaching the rear leaf spring 34 to the top of the central portion 35 of the spring support 31. Spaced inwardly from the rear edge of the spring support 31 and centrally between the end portions 36 and 37 is a hole 40 in which an aluminum sleeve 41 is tightly fitted. The sleeve 41 accommodates an electrical clip connection.

The electromagnet assembly 12 includes a pair of electromagnets 42 and 43. The electromagnets 42 and 43 each comprise a spool 44 on which an electromagnet coil 45 of insulated wire is would and a soft iron core 46 which extends through the hollow hub of the spool. The electromagnets are supported on top of vertically stacked plates 47 and 48 which are supported on top of the base 18. The plate 47 is made of ingot iron and forms part of the magnetic circut which includes the soft iron cores 46,46 of the electomagnets 42 and 43. The plate 48 is made of Rulon which serves as a noise retardant and reduces the noise of the instrument when it is in operation. The base 18, and the plates 47 and 48 have two sets 49 and 50 of holes each set of which is aligned with a threaded bore 51 in the base of a different one of the soft iron cores 46 of the electromagnets 42 and 43. A separate headed screw 52 is inserted from beneath the base 18 through each set of holes and is screwed into the threaded bore in the base of the core 46 for each electromagnet to firmly secure the electromagnet cores on the plates 47 and 48 and base 18.

The armature assembly 13 includes an armature bar 53 of ingot iron which is supported above the soft iron cores 46 of the electromagnets 42 and 43 by the rear leaf spring 34. The spring 34 is secured at its rear end on top of the spring support 31 and it is fastened at its front end to the armature bar 53 by screws 54 of which there are two in spaced transverse alignment. Just forward of the front end of the rear leaf spring 34, the armature bar has an upwardly inclined ramp 55 the upper face of which is substantially parallel with the longitudinal axis of the slot 27 in the elongated enlargement 26 of the frame sideplates 23,23. The ramp 55 supports on its upper face the rear end of an elongated linear front leaf spring 56. The front leaf spring 56 extends forwardly and upwardly from the ramp 55 in parallel with the face of the ramp and has a silver switch contact 58 riveted thereon adjacent its forward end. The front leaf spring 56 is removably fastened to the ramp 55 by a pair of transversely spaced screws 57. The bottom surface 59 of the armature bar 53 is planar and is normally supported by the rear leaf spring 34 above the soft iron core 46 of the rear electromagnet 42 with an airgap 60 there between. An adjustment of the space between the bottom 59 of the armature and the tops of the electromagnet cores 46 can be made by loosening the screws 32 and 33 securing the spring support 31 to the frame and tilting the front end of the spring support 31 up or down about the rear pivot screws 33. Once the desired airgap 60 is obtained the screws 32 and 33 are tightened to hold the rear leaf spring 34 and the armature bar 53 in the desired position. At the front end of the armature bar 53 is an enlarged head portion 61 which is of uniform rectangular cross section and is of a width sightly less than the distance between the frame side plates 23,23. The opposite ends of the head portion 61 extend laterally beyond the sides of the narrower rear portion 62. A vertically oriented alignment bore 63 extends perpendicularly through the head portion 61. It is provided so that the operator can adjust the position of the armature bar to line up the alignment bore 63 with an axial bore 64 provided in the top end of the iron core 46 of the electromagnet 43. When the alignment bore 63 and the bore 64 are aligned the armature bar is properly positioned relative to the electromagnets 42 and 43 except for adjustment of the air gap 60. A bearing block 65 of Oilite or other suitable bearing material is secured to the front end of the armature bar 53 by a screw 66 inserted from the recess 67 through a bore 68 at the rear of the bearing block into a threaded bore extending inwardly into the head portion 61 from the front thereof. The bearing block 65 has forwardly projecting ears 70 and 71 on opposite sides of the recess 67. The ears 70 and 71 have axially aligned grooves 72 and 73 formed therein extending inwardly from the front face thereof to receive axially aligned cyclindrical pivot studs 74,74 therein which are part of the needle holder assembly 15.

The needle holder assembly 15 includes the needle holder block 75 which has a longitudinal bore 76 therethrough in which is secured the shaft 77 of a tattooing needle assembly 17 by a set screw 79. The needle holder block 75 is a rectangular prism which fits within the rectangular prismatic recess 67 and is pivotally supported therein by the laterally projecting pivot studs 74,74 extending from opposite sides of the needle holder block and supported in the grooves 72,73 of the bearing block 65.

The tattooing needle assembly 17 comprises the elongated linear needle shaft 77 and one or more small needles 78 soldered to the end of the needle shaft opposite the end which is fitted in the needle holder block 75. Different tattooing needle assemblies may be used interchangably depending upon the nature of the work which is to be performed. Two commonly used tattooing needle assemblies are the outliner needle assembly and the shader needle assembly. In the outliner needle assembly five needles are soldered together in parallel in a perfect circle. In the shader assembly six needles are aligned side-by-side in line abreast and soldered together with adjacent needles contacting each other.

The needle assembly 17 shown in FIG. 1 is an outliner assembly which is slidably mounted to reciprocate within the outliner hand-piece or outliner needle guide assembly 16 in response to vibration of the armature assembly 13 and needle holder assembly 15 by the electromagnet assembly 12. The outliner needle guide assembly 16 comprises a knurled outer cylinder of hand piece 80, an upper inner cylindrical extension 81 projecting upwardly from the upper end of the outer tube 80, a collar 82 on the upper extension 81, a lower inner cylindrical extension 83 projecting downwardly from the lower end of the hand piece 80, a downwardly tapered tubular nose piece 84 fitted at its upper end within the lower extension 83 and a linear needle guide member 85 secured within and projecting downwardly from the nose piece 84. The upper and lower extensions 81 and 83 fit snugly within cylindrical bores 81' and 83' provided in he upper and lower ends respectively of the handpiece 80 and are coaxial therewith. They are retained in the hand piece 80 in adjusted position by set screws 86 and 87 respectively. The nose piece 84 is soldered in the bottom end of the lower extension 83 and the needle guide member 85 is soldered in the bottom end of the hollow nose piece 84. Holes 88 and 89 are provided in the upper extension and in the nose piece 84 respectively to facilitate cleaning and inspection of the needle guide assembly. The collar 82 is secured over the upper extension 81 at a selected location below the upper end of the extension by a set screw 90, which is screwed into the threaded bore 90' that extends radially through the collar until it is seated tightly against the upper extension 81. On the opposite side of the collar from the set screw 90 and 180° displaced therefrom is a longitudinal key slot 91 with key 92 fixed therein. The key 92 extends upwardly from the collar and fits within a locater keyway 93 provided within a needle guide assembly holder 94.

The needle guide assembly holder 94 is a plastic block of sustantial thickness which is hinged to the front of the base 18 by a plurality of transversely spaced, rearwardly extending knuckles 95 which interfit with a plurality of transversely spaced, forwardly extending knuckles 96 on the front end of the base 18 and which are joined thereto by a pintle 97 extending through the two sets of knuckles. The front end 94' of the holder 94 is split by a slot 98 opening into a cylindrical bore 99 which receives the upper end of the upper extension 81. A transverse bore 100 is provided transversely through the bifucated front end 94'. The bore 100 is threaded on one side of the slot 98 and is enlarged on the other side of the slot to receive a headed screw 101 which is inserted from the side with the enlarged bore and is threaded into the threaded bore to draw the bifucated front end together and tighten the holder about the upper extension 81. The needle guide assembly holder 94 and the collar 82 with its key 92 which fits in the keyway 93 in the holder 94 facilitates removal of the needle guide assembly 16 from the rest of the tattooing apparatus 10 for cleaning and sterilization by loosening the screw 101 and sliding the needle guide assembly 16 downwardly until the upper extension 81 is free of the bore 99 in the holder 94. The needle guide assembly 16 may be quickly reassembled in proper alignment in the holder 94 by reinserting the end of the tubular extension 81 in the bore 99 and turning the assembly until the key 92 lines up with the key slot 93, then pushing the entire assembly 16 toward the holder 94 until the collar 82 abuts against the underside of the holder 94 (See FIG. 8). The holder 94 is then tightened upon the tubular extension 81 by tightening the screw 101.

Figure 8:
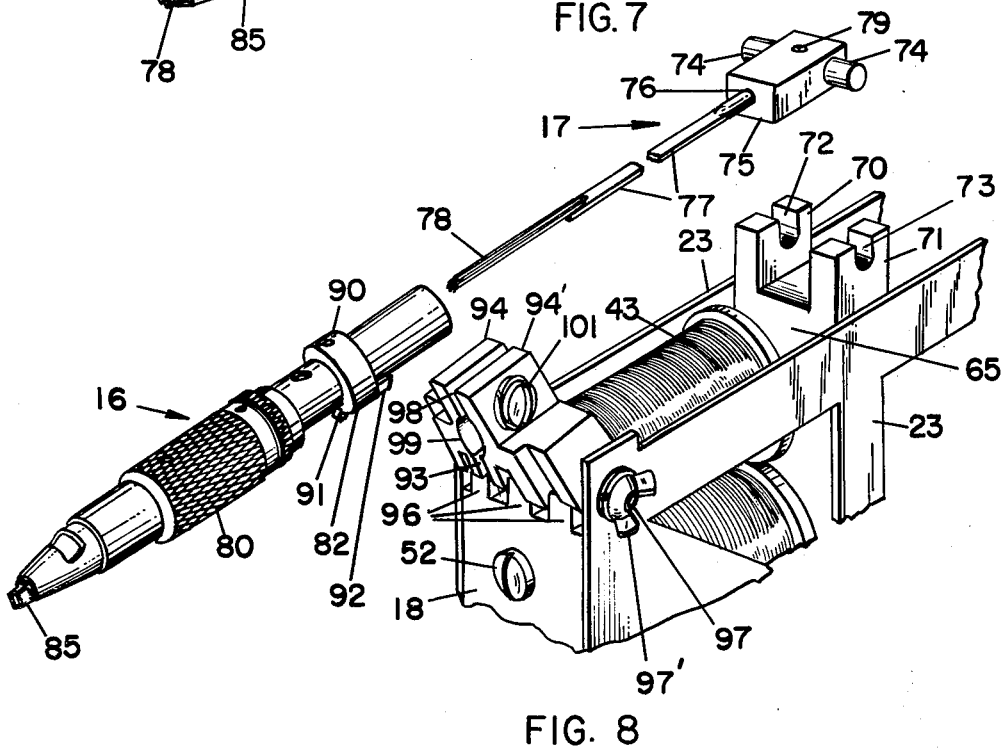
FIG. 8 is a fragmentary perspective view of the invention shown in FIG. 1, showing the needle guide assembly holder tilted to position for disassembly of the needle assembly and needle guide assembly from the remainder of the apparatus, and showing the needle assembly and needle guide assembly separated.

The needle assembly 17 is preferably disassembled from the needle guide assembly 16 prior to removing the needle guide assembly from the holder 94. In order to do this, the wing nut 97' on the pintle 97 is loosened so that the holder 94 may be pivoted down as seen in FIG. 8 and the needle assembly and its holder block 75 is swung out of the bearing block 65. Once the needle holder block 75 is free of the bearing block 65, the needle shaft 77 with the needle holder block 75 still attached may be pulled out of the needle guide assembly 16. Reassembly of the needle assembly with the needle guide assembly and the bearing block 65 is performed by reversing the steps just described.

Figure 7:
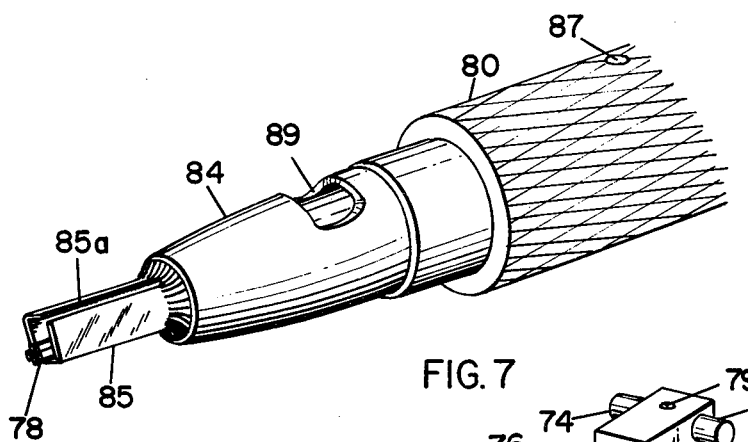
FIG. 7 is an enlarged perspective view of the lower end portion of the outliner needle guide assembly of the apparatus shown in FIG. 1 and showing the lower ends of the outliner needles.

In order to hold the needle assembly 17 with needle block 75 and its stub shafts 74 firmly seated in the grooves 72 of the bearing block 65, one or more elastic bands 140 are placed in front of the needle shaft 77 with the ends thereof looped over the screws 22'. The screws 22' have collars or spacers underneath their heads to space the heads from the side plates 23 on each side of the apparatus. The end loops of the rubber band 140 pass around the collars under the heads of the screws 22' and are retained in place by the screw heads. The rubber band 140 also serves to pull the needle shaft 77 inwardly so that the needles 78 slide against the back side of the needle guide 85 opposite the slot 85a (see FIG. 7).

The interrupter switch assembly 14 includes the movable switch contact 58 mounted on top of the front leaf spring 56 as previously described, an elongated cylindrical adjustable switch contact 102, and a rectangular prismatic plastic molding block 103 having a cylindrical bore 104 therethrough in which the fixed switch contact 102 is adjustably mounted in substantially axial alignment with the contact 58. The mounting block 103 is divided into rectangular front and rear portions 105 and 106 respectively which are secured together with screw fasteners 107. The mounting block 103 is adjustably supported on top of the tattooing apparatus 10 by a headed screw 108 which extends through the slots 27 in the side plates 23,23, and a transverse bore in the mounting block 103, and is secured by wing nut 108'. When the nut 108' is loosened, the block 103 may be adjusted fore and aft within the limits of the elongated slots 27 and it may be tilted about the axis of the screw 108 on each side of the block. The block 103 is divided along a perpendicular plane which is parallel to the front and rear faces of the block and which extends diametrically through the bore 104. The size of the bore 104 is such that when the front and rear portions of the block 103 are secured together with the elongated cylindrical contact 102 in the bore 104, and tightened, the contact 102 is tightly held in adjusted position. The contact 102 is of a length substantially greater than the length of the bore 104 so that it may be adjusted with its opposite ends projecting from the top and bottom of the block 103. The contact 102 is adjusted longitudinally within the bore 104 until there is a proper gap between the bottom planar face of the contact 102 and the adjacent face of the contact 58 when the switch 14 is open. An electric circuit connector 109 of copper or other conductive material is attached at the upper end of the contact 102 by means of a screw 110 threaded into the threaded axial bore 111.

In accordance with this invention, the apparatus will be provided with a set of three rear leaf springs 34 of different lengths and a set of three front leaf springs 56 of different lengths—short, medium, and long. By way of example only, the set of rear leaf springs will include springs of lengths 1 11/32", 1 19/32" and 1 27/32" respectively; the set of front leaf springs will include springs of length 1 5/16", 1 19/32" and 1 27/32" respectively. The springs 34 and 56 are made of beryllium copper. The rear leaf springs 34 are all normally flat rectangular plates of the same thickness and width but of different lengths. The front leaf springs 56 each include a rectangular rear or attachment portion and a tapered free end portion. All of the front leaf springs are of the same thickness, their rectangular attachment portions are of the same width and length, and their tapered free end portions have opposite sides which converge uniformly to the free end which is of the same width in all of the springs. Only the lengths of the tapered portion varies with the several different front leaf springs, thus providing the variation in the overall length of the different front leaf springs. By selecting different combinations of lengths of front and rear leaf springs 56 and 34 from the two sets provided, an operator has the option of nine different combinations giving a wide range of possibilities. There is a positive correlation between the lengths of stroke (that is, the distance of the gap between the switch contacts 58 and 102) and the length of the springs on any tattoo machine. A longer spring, fore and aft, allows the operator to increase the length of the stroke, and a shorter spring fore and aft permits the operator to decrease the length of stroke. The execution of large tattoos over fleshy areas of the anatomy (for example, the back, stomach, thighs, ets.) require a stroke of maximum length, because using a short stroke on such areas where one cannot get the skin taut, causes the needles to hang up, or hook. When rendering tattoos on arms where the operator can hold the skin taut with a free hand, a short stroke is generally preferred.

The change of length of the rear spring 34 requires readjustment of the rear spring support 31 by loosening the screws 32 and 33 and sliding the support 31 forwardly or rearwardly depending on the length of the spring 34 selected. The location of the armature bar 53 as previously described is established by aligning the alignment bore 63 in the armature with the bore 64 in the core 46 of the electromagnet 43, therefore the location of the armature 53 remains the same irrespective of the different spring combinations used. Changing the length of the front leaf spring 56 requires readjustment of the upper contact mounting block 103 in order to axially align the upper contact 102 with the lower contact 58.

An aluminum spool 113 is supported between the pair of rear extension plates 19,19 by slotted head screws 114,114 on opposite sides of the plates. The screws 114,114 extend through the plates and are screwed into a threaded bore 113, which extends axially through the spool 113. A transverse bore 115 extends through the longitudinal center of the spool 113 for the reception of one prong of a special double pronged electrical connector 122 (see FIG. 9). Copper electrical clips 116 and 117 are supported on opposite sides of the spool 113 against the flanges of the spool by screws 114,114. Electrical insulation washers 118 are interposed between the connectors 116 and 117 and the rear extension plates 19,19. Similar insulation washers 118 are interposed between the heads of screws 114,114 and the outside of the plates 19,19.

Figure 3:
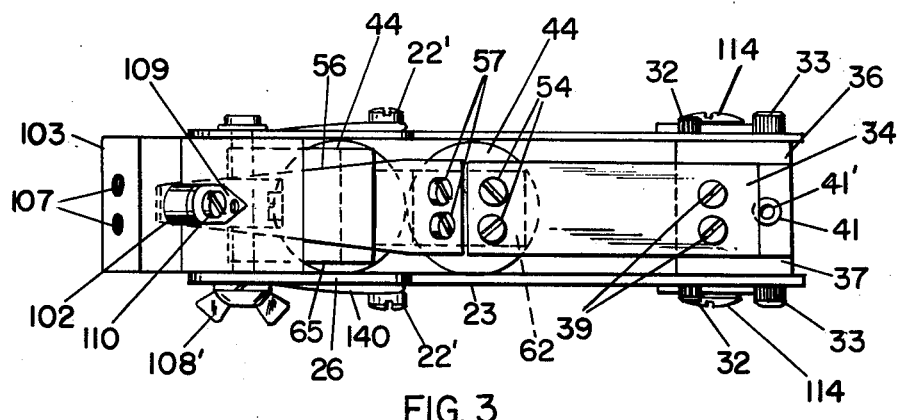
FIG. 3 is a top plan view of the invention.
Figure 4:
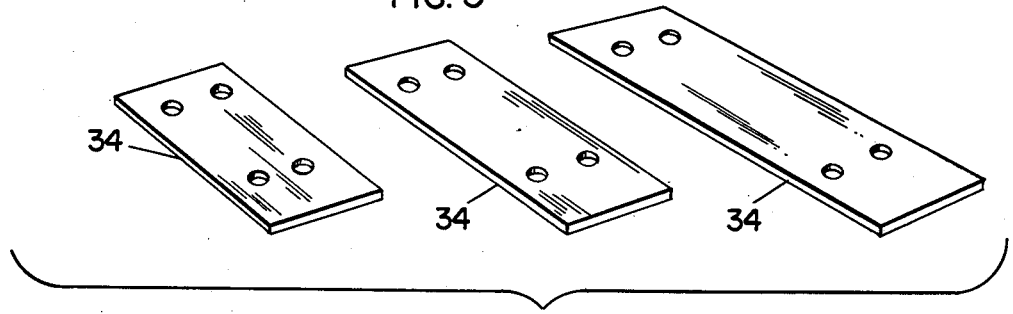
FIG. 4 is a perspective view of a set of armature support springs of different lengths for use selectively in the invention.
Figure 5:
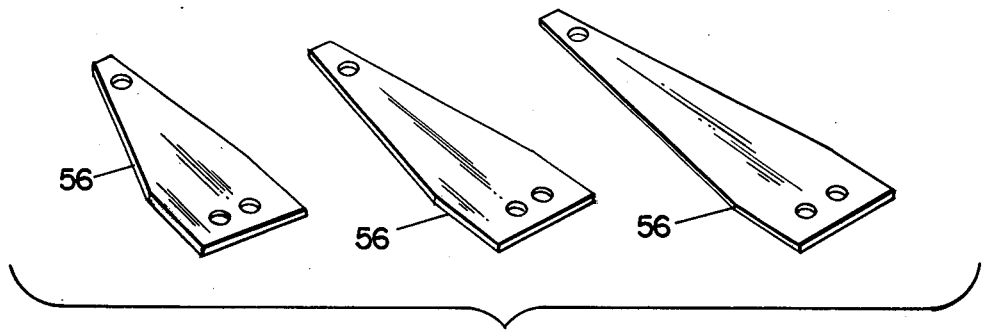
FIG. 5 is a perspective view of a set of front leaf springs of different lengths for use electively in the invention.
Figure 9:
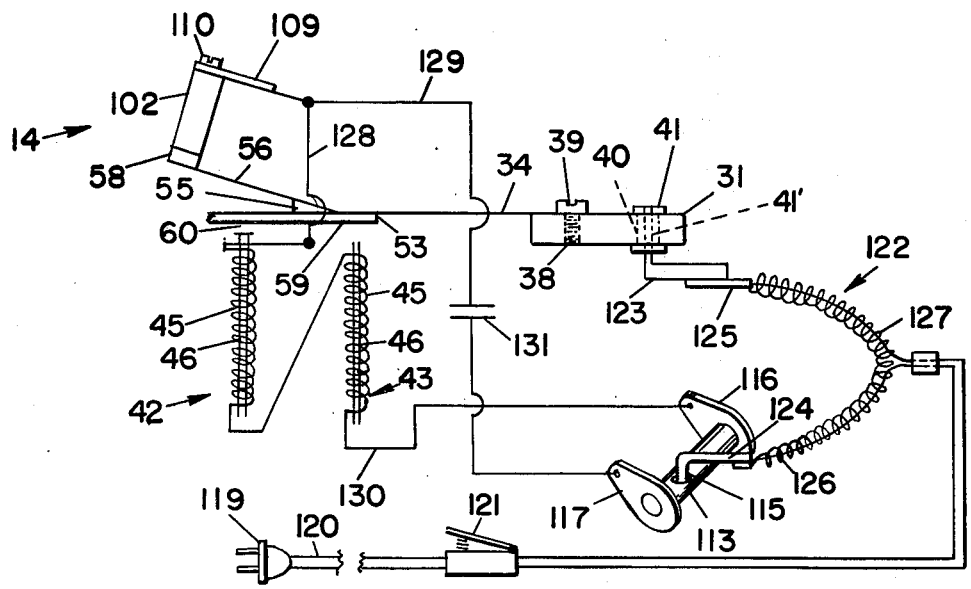
FIG. 9 is a diagrammatic view of the electrical circuit portions of the invention.

The electric circuit for the apparatus 10 is shown in FIG. 9. The power supply circuit includes a power plug 119 on the end of a two conductor power cord 120, a foot switch 121 for making and breaking the power circuit at the will of the operator, and a special spring clip connector 122 which is easily attached and detached from the tattooing apparatus 10. The spring clip connector 122 comprises a pair of L-shaped prongs 123 and 124 of circular cross section adapted to fit in the hole 41' of the aluminum plug 41 in the spring support 31 and in the transverse bore 115 in the aluminum spool 113. The prongs 123 and 124 are soldered to the ends of conductors 125 and 126 which are the individual conductors of the two conductor power cord 120. The conductors 125 and 126 are inserted through opposite ends of a a coil spring 127 and they emerge from inside of the spring approximately midway of its length. The spring 127, which is normally linear, when bent as shown in FIG. 3 within its elastic limit, urges the prongs 123 and 124 apart and holds them secure in the holes 41' and 115 respectively. The electric circuit of the apparatus from the prong 123 to prong 124 includes the aluminum plug 41, the armature spring 34, the movable contact spring 56 of the interrupter switch 14, the interrupter switch 14, connector clip 109, conductor 128, the coils 45,45 of the electromagnets 42 and 43, conductor 130, copper clip 116, and aluminum spool 113. A capacitor 131 is connected in circuit 129 across the interrupter switch 14 and the electromagnets 42,43 from clip 109 to clip 117 to reduce arcing across the spring contacts 58 and 102 as the interrupter switch 14 makes and breaks.

Figure 6:
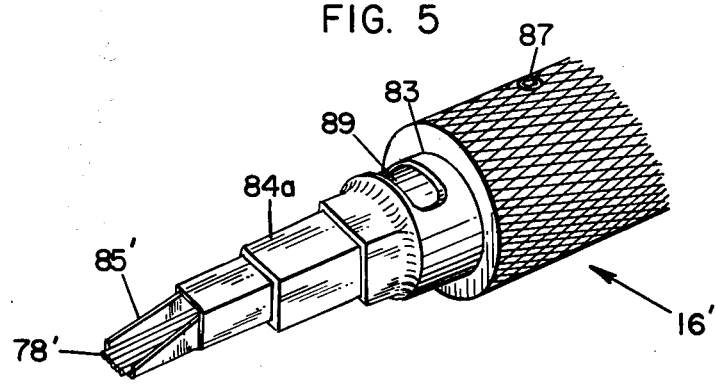
FIG. 6 is an enlarged perspective view of the needle guide end portion of a shader needle guide assembly for use interchangeably with the outliner needle guide assembly shown in FIGS. 1, 7 and 8 showing the ends of the shader needles.

A fragmentary perspective view of a shader needle guide assembly 16' is shown in FIG. 6. Only the portion of the shader needle guide assembly including the lower portion of the hand piece 80, its lower tubular extension 83, a tapered nose piece 84a, a shader needle guide 85', with shader needle group 78' therein are shown because the upper portion of the shader needle guide assembly is exactly like the outliner needle guide assembly shown in FIGS. 1 and 8. The shader needle group 78' comprise a plurality of parallel needles arranged in line abreast. The individual needles are contiguous to adjacent needles and they are soldered at their ends which are remote from the exposed pointed ends shown in FIG. 6 to one end of a needle shaft 77. The needle guide 85' is soldered in the outer end of the tubular nose piece 84a; it is channel shaped having a flat back wall against which the needles 78' slide, and a pair of parallel opposite sides normal to the back side which confine the needles 78' against lateral displacement. The front side of the needle guide is open to expose the needles 78' to the view of an operator. The correct angular position of the needle guide 85' is such that a plane perpendicular to the back side of the needle guide and including the longitudinal center line of the back side would pass through the center of the holes 89 and 87 shown in FIG. 6 as well as through the centers of the holes 86 and 88 in the upper portion of the tubular needle guide assembly as shown in FIG. 1. The holes 89, 87, 86 and 88 would be aligned in the front of the assembly and would be 180 degrees displaced from the locator key 92 secured in the collar 82 on the backside of the needle guide assembly. The nose piece 84a comprises a plurality of square sectioned tubes of progressively smaller size, the largest square sectioned tube having its inner end soldered in the outer end of the lower extension 83, the next largest tube having its inner end telescoped in the outer end of the largest tube and soldered therein, and so on until the smallest tube having its inner end telescoped and soldered in the outer end of the next larger tube. The shader needle guide assembly 16' and shader needles 78' would be used interchangeably with the outliner needle guide assembly 16 and outliner needle assembly 17 shown in FIGS. 1, 7 and 8. The capability of the quick interchange of different needle guide and needle assemblies and the securement of the selected assemblies in the needle guide holder 94 and needle bearing block in correct position is an important advantage of the invention.

In use, an operator holds the electric marker device 10 (See FIG. 1) in one hand by the tubular hand piece 80. The needles 78, or other selected needle group, are dipped in pigment, and the operator is ready to begin tattooing or other marking operation. The apparatus is energized by closing the foot switch 121 (FIG. 9) which is provided in order to leave the operator's hands free for manipulation of the marker device 10. Once electric power is applied to the device, the electromagnets 42 and 43 are energized and attract the armature bar 53. The attraction of the armature bar 53 to the electromagnets separates the contacts 58 and 102 of the interrupter switch 14, thereby de-energizing the electromagnets 42 and 43. The armature bar 53 is then returned to the normal position by the armature support spring 34 and the interrupter switch 14 is again closed restoring the continuity of the circuit to the electromagnets 42 and 43. The electromagnets thereby are alternately energized and de-energized repeatedly as long as the foot switch 121 is closed. The armature bar 53 oscillates and its oscillation causes the needle assembly 17 to reciprocate in the needle guide assembly 16.

An important feature of this invention is the pivoted needle guide assembly holder 94 which makes it very simple to at any time increase or decrease the pressure of the needle against the tip by one simple movement either upward or downward, thereby maintaining the ideal friction between the needles and the needle guide tip at all times.

The needle shaft 77 is preferably cylindrical, particularly at its upper end, so that it may be received in the cylindrical bore 76 of the needle holder block 75 and rotated until the needles 78 are properly adjusted relative to the needle guide 85. The needle shaft 77 may be flattened intermediate its ends by filing off metal on its opposite sides inorder to make the shaft more flexible to bend in a plane extending through the longitudinal axis of the needle shaft and parallel to the side walls 23 of the frame assembly 11. The tension of the elastic band 140 draws the needle shaft 77 rearwardly toward the back side of the needle guide assembly 16 (see FIG. 1). The degree of flexibility of the needle shaft 77 can thus be increased at the option of a particular operator. The needle assembly 17, including the needle shaft and needles, is preferably made of stainless steel or other suitable stainless metal which may be sterilized.

While in the foregoing there has been described and shown a preferred embodiment of the invention, various modifications and equivalents may be resorted to within the spirit and scope of the invention as claimed.

What is claimed is:

1. An electric marker device comprising a frame, an armature bar, adjustable resilient support means for supporting said armature bar on said frame for oscillation thereon, electromagnet means supported on said frame for oscillating said armature, a control circuit for energizing said electromagnet means, an interrupter switch in said control circuit for cyclically energizing and de-energizing said electromagnet means in response to the oscillation of said armature bar, an elongated hollow needle guide assembly having a supported end and a free end, a needle guide assembly holder means pivotally supported on said frame for detachably supporting said supported end of said needle guide assembly in a predetermined position, a needle assembly comprising an elongated needle shaft and needle marker means affixed to one end of said shaft, said needle assembly being reciprocatably mounted in said hollow needle guide assembly with said needle marker means projecting from said free end and with said needle shaft projecting from said supported end, a needle assembly holder removably secured to the end of said needle shaft opposite said needle marker means, and bearing means on said armature bar for pivotally supporting said needle assembly holder and for reciprocating said needle assembly holder and needle assembly as said armature bar is oscillated by said electromagnet.

2. The marker device of claim 1 wherein said needle guide assembly includes a tubular handpiece with tubular extensions projecting from both ends of said tubular handpiece, one of said extensions being the supported end of said needle guide assembly, a collar slidably supported on said one tubular extension at a predetermined distance from the end thereof remote from said tubular handpiece, a locator key supported by said collar in parallel with the longitudinal axis of said one tubular extension, a locator keyway in said needle guide assembly holder means in which said locator key is slidably received when said supported end is supported in said needle guide assembly holder means, and means for adjustably securing said collar on said one tubular extension with said locator key in a predetermined angular position so that said needle guide assembly may be repeatedly removed from said needle guide assembly holder means and replaced therein in substantially the same predetermined location each time once the adjustment of said collar on said one extension has been made.

3. The marker device of claim 2 wherein the other of said tubular extension has a tapered hollow nose piece secured therein, and a needle guide secured in the tapered end of said nose piece.

4. The marker device of claim 3 wherein said tubular extensions are removably telescoped in said tubular handpiece from opposite ends thereof, said tubular handpiece having set screws extending radially therethrough for locking said tubular extensions in said hand piece.

5. The marker device of claim 4 wherein said needle guide assembly includes a set of different needle assemblies, each having a needle shaft and needle marking means differing from the needle marking means of other needle assemblies of said set for performing different marking functions, and a corresponding set of different needle guides assembled in a nose piece and a tubular extension, one of the needle assemblies being selected for performing a specific function and having the end of its needle shaft remote from its needle marking means removably secured in said needle assembly holder, and one of said needle guides with attached nose piece and tubular extension being selected from said set for cooperation with said selected needle assembly.

6. The marker device of claim 5 wherein said set of different needle assemblies includes a tattooing shader needle assembly and a tattoing outliner needle assembly, said shader needle assembly marking means comprising a plurality of parallel needles arranged in line abreast with adjacent needles contiguous and having needle points uniformly aligned in a common plane, said outliner needle assembly marking means having a plurality of parallel needles arranged in a circle with adjacent needles contiguous and having all needle points located in a circle in a common plane, said needle guide for said shader needle assembly being channel-shaped and having a flat surface upon which said needles of said shader needle marker means slide, and opposite side walls perpendicular to said flat surface, said side walls being separated by a distance slightly greater than the distance across the multiple needles in line abreast to confine said multiple needles for linear reciprocation therein, said needle guide for said outliner needle marker means being a square tube having one corner of said tube removed to provide a slot for observation of said outliner needle marker means.

7. The marker device of claim 3 wherein said tapered hollow nose piece comprises a series of progressively smaller cross-sectioned tubes, said tubes of said series each having inner and outer ends, the largest tube of said series having its inner end secured within the outer end of said other tubular extension, and its outer end projecting from the outer end of said other tubular extension, and each of the other tubes of said series having its inner end secured within the outer end of the next larger tube of the series with its outer end projecting from the outer end of said next larger tube, said needle guide being tubular and having an inner end and an outer end, said inner end of said needle guide being secured in the outer end of the smallest tube of said series of tubes in said nose piece and having its outer end projecting outwardly from the outer end of said smallest tube, said needle guide having one side open to permit viewing of the needle marking means within said guide.

8. The marker device of claim 7 wherein each of said tubes of said series is of uniform cross section throughout its length.

9. The marker device of claim 8 wherein each of said tubes of said series has a square cross section.

10. The marker device of claim 8 wherein each of said tubes of said series has its inner end soldered in the outer end of the next larger tube and said needle guide having its inner end soldered in the outer end of the smallest tube of said series.

11. The marker device of claim 1 wherein said needle guide assembly has longitudinally spaced apertures therein for flushing a cleaning fluid through the hollow interior thereof.

12. The marker device of claim 1 wherein said frame comprises a rectangular prismatic base, a pair of side plates each secured on an opposite side of said base from the other plate and extending upwardly from said base in parallel with the other side plate, each of said side plates having a base portion, a front strip portion with an enlarged head portion thereon, a rearwardly extending top strip portion which is normal to said front strip portion and which extends rearwardly therefrom from a position intermediate said head portion and said base portion, a longitudinal slot formed in said rearwardly extending strip portion forward of the rear end thereof, a diagonal brace portion extending from said base portion and connected with said rearwardly extending strip portion, said head portion being elongated and inclined upwardly in the front and downwardly at the rear of said front strip, an elongated slot in said head portion and similarly inclined, said electromagnet means being supported on said base between said side plates, said adjustable resilient support means for supporting said armature including a spring support adjustably secured between the top strip portions of said pair of side plates, headed screw fastener means extending through said elongated slot of said top strip portion of each side plate into said spring support for securing said spring support in adjusted position within the confines of said slots, said headed screw fastener means including a rear set of two screws of a diameter approximately equal to the width of said slot in said top portion, and a front set of two screws of a diameter substantially less than the width of said slot, each screw of each set being secured to an opposite side of said spring support from the other screw of the same set, said screws of said front and rear sets when loosened allowing longitudinal adjustment of said spring support fore and aft relative to said top strip, and said screws in said front set permitting the front of said spring support to tilt up and down about said rear set of screws which function as pivot means, an elongated leaf spring having one end secured on said spring support and its other end projecting forward of said spring support and attached to said armature bar, said leaf spring normally holding said armature bar spaced above said electromagnet means by a predetermined amount.

13. The marker device of claim 12 wherein said interrupter switch includes an elongated adjustable switch contact, adjustable mounting means for mounting said adjustable switch contact to said elongated head portion, and a front leaf spring having one end secured on top of said armature bar and a free end projecting forward of said armature bar and supporting a movable switch contact facing said adjustable switch contact, said adjustable switch contact mounting means having parallel opposite sides and a bore therethrough in which said elongated adjustable switch contact is adjustably mounted to project out of said bore toward said movable contact a selected distance, a pair of screw fasteners extending from opposite sides of said mounting means, each screw of said pair extending through the slot in said head portion of said frame on one side thereof for adjustably securing said mounting means to said frame, said pair of screw fasteners when loosened permitting said mounting means to slide fore and aft relative to said head portion and allowing said mounting means to tilt about said screw fasteners, said pair of screw fasteners when tightened securing said mounting means in adjusted position.

14. The marker device of claim 12 together with a set of multiple elongated leaf springs of different length which may be used interchangeably for the support of said armature bar from said spring support at the selection of an operator.

15. The marker device of claim 13 together with a set of front leaf springs of different length which may be used interchangeably for the support of said movable switch contact from said armature bar at the selection of an operator.

16. The marker device of claim 1 wherein said armature bar and said electromagnet means have locator means for properly locating the position of said armature bar with respect to said electromagnet means.

17. The marker device of claim 1 wherein said needle assembly holder is a block having a longitudinal bore therethrough and has a pair of axially aligned transverse stub shafts extending from opposite sides thereof, said bearing means has a front face extending forward of said frame with axially aligned transverse grooves therein and a recess between said grooves for receiving said holder with said stub shafts seated in said grooves, said needle shaft being slidably mounted in said longitudinal bore of said needle holder block, and fastener means for securing said needle shaft in said needle holder block in an adjusted position.

18. The marker device of claim 17 wherein said needle shaft is also rotatably adjusted in said needle assembly holder in a predetermined angular position.

* * * * *